United States Patent [19]

Breuker et al.

[11] 4,447,775
[45] May 8, 1984

[54] APPARATUS AND METHOD FOR CONTINUOUS PH MONITORING

[75] Inventors: Stephen J. Breuker; Harold L. Richmann, both of Fremont, Mich.

[73] Assignee: Gerber Products Company, Fremont, Mich.

[21] Appl. No.: 397,727

[22] Filed: Jul. 12, 1982

[51] Int. Cl.³ .................... G01N 27/38; G01N 27/56
[52] U.S. Cl. .................... 324/438; 204/1 T; 204/402; 204/409
[58] Field of Search ............ 324/438; 204/195 G, 204/195 R, 1 H, 409, 402

[56] References Cited

U.S. PATENT DOCUMENTS 2,768,135 10/1956 Adelson ......................... 204/195 R
3,997,420 12/1976 Buzza ............................. 204/195 P
4,160,714 7/1979 Andersen et al. ............... 204/195 R Primary Examiner—G. L. Kaplan
Attorney, Agent, or Firm—Townsend and Townsend

[57] ABSTRACT

An apparatus and method are disclosed for the continuous monitoring of pH in a fluid stream flowing at a low volumetric flow rate. The stream is directed through an enclosed conduit with a glass electrode sealed therein. The conduit wall facing the electrode has contour approximately complementary in shape to the sensing surface of the electrode with a narrow gap between the opposing surfaces through which the fluid passes, forcing rapid and uniform flow of the fluid over the electrode surface. Continuous operation is thereby permitted for extended time periods without substantial fouling of the surfaces.

8 Claims, 3 Drawing Figures

U.S. Patent May 8, 1984 Sheet 1 of 2 4,447,775
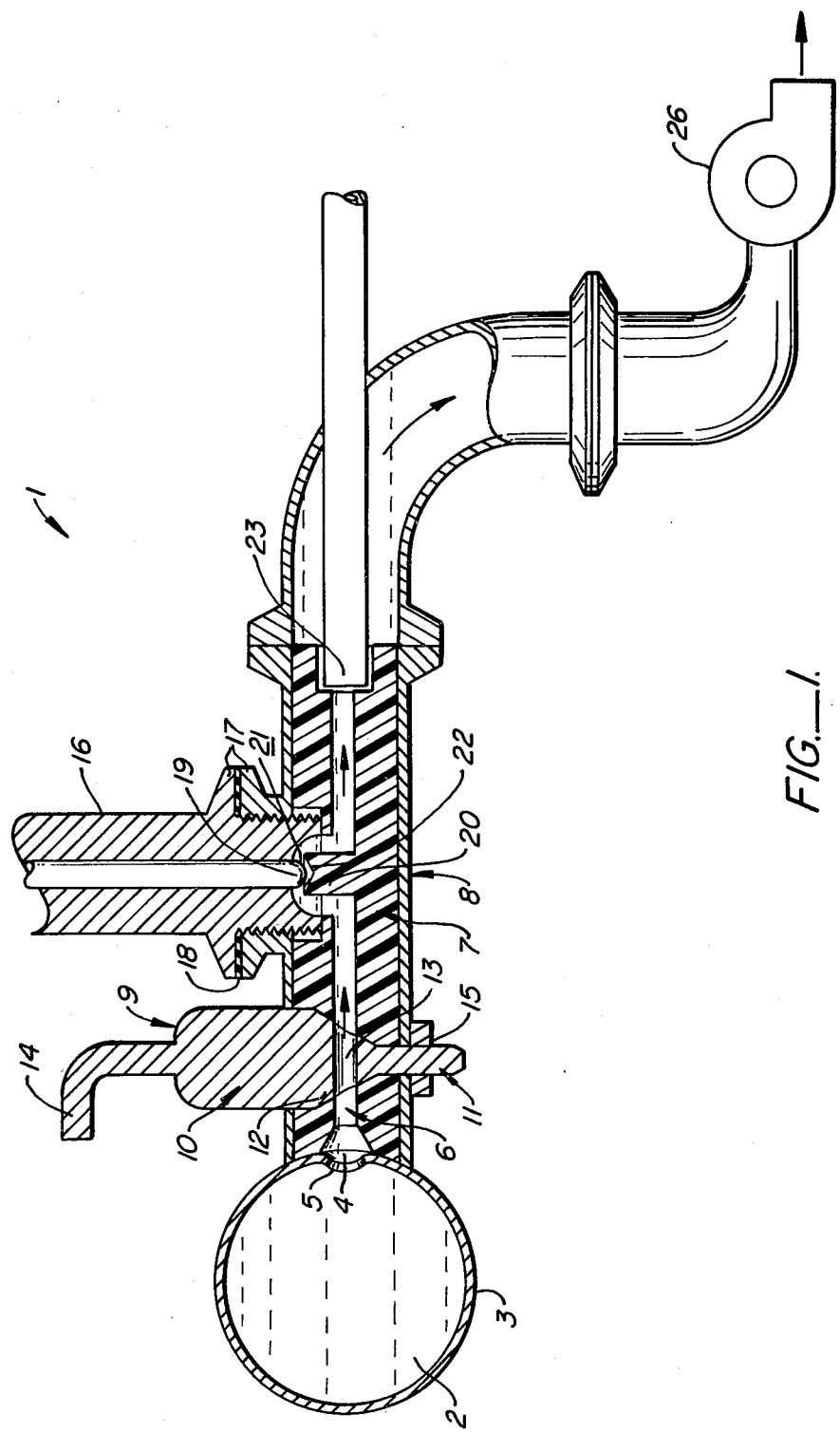
FIG._1.

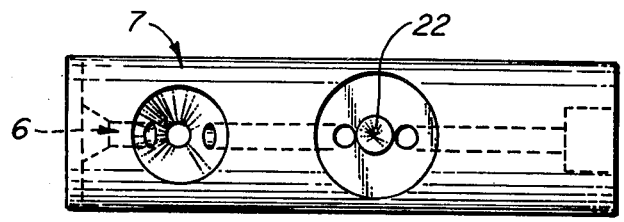
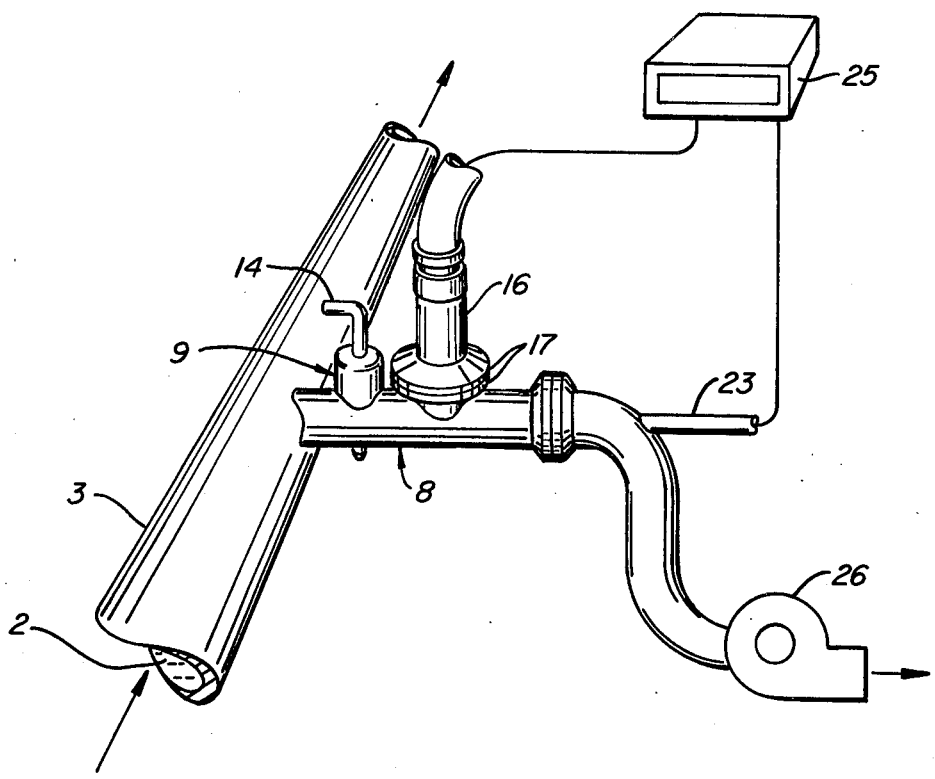

APPARATUS AND METHOD FOR CONTINUOUS PH MONITORING

BACKGROUND OF THE INVENTION

In many continuous chemical processes, the continuous monitoring of pH in a stream of flowing fluid is necessary to ensure process control and product quality. Flow-through pH monitoring stations are commonly used for this purpose.

In some applications, however, the placement of a pH electrode in the process stream is undesirable due to the risk of breakage of the electrode and resulting contamination of the process stream. In the food process industry, for example, all possibility of product contamination must be avoided. Glass electrodes, normally the most useful type of process pH electrode, can thus be used only if placed in a side stream which is bled off the process stream and then directed to waste once it has passed the electrode.

Current devices for on-stream pH monitoring require flow rates of 0.25 gallons per minute (1.0 liters per minute) or higher in order to provide an accurate reading. At lower flow rates a lag time exists between the sample point and the electrode signal and the flow passages and electrodes quickly become fouled, particularly when the process fluid is a suspension. High flow rate bleeds are undesirable where the wasted portion represents a substantial economic loss. This is particularly true in the food processing industry where the wasted portion of the process stream cannot be recovered for sale.

There is therefore a need for a flow-through pH-measuring device designed for installment in a bleed stream off the process line to be analyzed, capable of providing a reading substantially current with respect to the process line, yet permitting a low volumetric flow rate with minimum opportunity for fouling.

SUMMARY OF THE INVENTION

Apparatus and method are provided for continuous pH measurement in a stream of fluid flowing at a low volumetric flow rate. The fluid stream is drawn past a glass electrode through a channel, the inner surface of which is approximately complementary in shape to the surface of the electrode, with a gap therebetween sufficiently narrow to produce a fluid velocity sufficiently high to maintain substantially uniform flow over the electrode surface. The apparatus and method permit continuous operation for extended periods of time without the need for frequent shutdowns to clean fouled surfaces which result from fluid or particle retention.

The invention will be more readily understood by reference to the attached drawings.

BRIEF DESCRIPTION OF THE DRAWINGS

FIG. 1 is a sectional view of a sample conduit installed on a process line. The conduit comprises a sleeve surrounding a machined insert and fitted with a turn-off valve, a pH electrode, a temperature sensor and a metering pump.

FIG. 2 is a top view of the insert shown in FIG. 1.

FIG. 3 is a perspective view of the process line and sample conduit of FIG. 1 together with a pH meter.

DETAILED DESCRIPTION

In the drawings, the apparatus of the present invention is represented by the numeral 1 and the fluid stream of which pH determination is sought is represented by the numeral 2. The fluid may be either a liquid or a suspension. In suspensions the suspended matter should be uniformly dispersed to provide uniform flow and a representative sample. The flow conduit 3 carrying the stream is equipped with a small aperture 4 of diameter substantially less than that of the process conduit 3. The aperture is equipped with a scoop 5 on the downstream side thereof to divert a portion of the process stream 2 into the aperture. The aperture is positioned in the conduit 3 such that the process fluid completely fills the aperture.

The relative sizes of the process conduit 3 and the aperture 4 will determine in part what portion of the process stream will be diverted for pH measurement and subsequent drain to waste. Although the actual amount diverted is most desirably as small as possible, those amounts which will be considered acceptable will depend upon the volume and nature of the process stream. In a typical application, the diameter ratio of process conduit to aperture will range from about 5:1 to about 50:1, preferably from about 5:1 to about 15:1.

The fluid passing through the aperture 4 enters a sample conduit 6 which is defined by a passage drilled through a plug insert 7 of appropriate outer diameter to fit snugly within a sleeve 8 securely affixed to the wall of the process conduit 3. The insert 7 is removable from the sleeve 8 upon dissassembly of the latter, for ease of cleaning, and is constructed of a material which is readily machinable and can be easily cleaned. In food process applications, the insert material must also meet federal standards established by the Food and Drug Administration and the United States Department of Agriculture, even though the fluid passing therethrough goes to waste. A particularly useful material for this purpose is Teflon ® (trademark of E. I. Du Pont de Nemours and Co. for tetrafluoroethylene fluorocarbon polymers). A further advantage of Teflon is its self-sealing and low-friction properties.

An optional feature shown in the drawings is a shut-off valve 9 immediately downstream of the aperture 4, to permit removal and cleaning of the components of the apparatus without requiring total shutdown of the process. The valve consists of two coaxial cylindrical sections 10 and 11 of different diameters connected by a conically shaped section 12 equipped with a transverse passage 13 of diameter identical to that of the sample conduit 16. The insert 7 is machined to receive the entire conical section 12 and portions of the two cylindrical sections 10 and 11 in rotatable fashion along the common axis and in fluid-tight manner, such that by rotation of the valve the transverse passage 13 can be precisely aligned with the sample conduit 6. The valve is further equipped with a handle 14 to permit manual rotation and retaining means 15 to secure the valve snugly in place.

Downstream of the shut-off valve is a pH electrode probe 16 secured into the sample conduit sleeve 8 by conventional fluid-tight means consisting of a pair of mated flanges 17 and a gasket 18. The probe 16 contains a pH-sensing surface in the form of a glass bulb 19 which extends into the sample conduit 6. A flow diverter 20 in the sample conduit 6 forces the entire sample stream to flow over the exposed portion of the electrode 21 in close proximity thereto. This is accomplished by the configuration of the diverter, one face of which 22 is approximately complementary in shape to the exposed portion 21 of the electrode, leaving a gap between the electrode surface 21 and the complementary diverter face 22 of at most about 0.5 cm, preferably from about 0.05 cm to about 0.3 cm on the average. The optimal gap size is the smallest distance which will permit flow of the fluid stream therethrough without excessive pressure drop, friction or agglomeration of suspended matter, and at a flow rate high enough to provide a pH reading sufficiently current to be substantially representative of that of the point in the process fluid 2 immediately adjacent to the inlet aperture 4. Homogeneous liquids of low viscosity and suspensions with a fine particle size will permit the smallest size gaps, while viscous liquids and suspensions with a large particle size will require larger gaps. The appropriate gap size will thus depend on the character of the fluid stream.

The shape of the diverter face 22 which complements the shape of the pH-sensing surface 21 of the electrode 16 will vary depending on the type of electrode used. When a flat-surface electrode is used, the diverter face 22 will also be flat. When a bulb-shaped (spherical) electrode is used, the diverter face may be either concave to approximate the curvature of the electrode bulb (with an allowance for the gap) or inverse conical (as shown in FIG. 1) with a half angle appropriately selected to provide the closest conformity with the curvature of the bulb as averaged over the bulb surface.

Positioned within the sample conduit downstream of the electrode 16 is a temperature probe 23, optionally included to enhance the accuracy of the pH measurement. The conduit is machined to receive the probe end, leaving a narrow gap 24 between the probe and the conduit wall to promote rapid flow past the probe. In this way, fouling of the probe surface when the fluid is a suspension is prevented. Both the temperature probe 23 and the electrode 16 are wired to a pH meter 25. Finally, a conventional metered pump 26 is positioned downstream of the temperature probe 23 to draw fluid from the process stream 2 through the sample conduit 6. The pump rate should be high enough that the pH reading obtained by the pH electrode 16 is substantially current with respect to the point 5 in the process stream 2 from which the sample is taken. The pump rate should be slow enough, however, to minimize the volume of process fluid diverted per unit of time through the sample conduit. In general, the optimal pump rate will be within the range of about 0.5 to about 10.0 gallons per hour (2 to 40 liters per hour), preferably about 1.0 to about 5.0 gallons per hour (4 to 20 liters per hour), and most preferably about 1.0 to about 3.0 gallons per hour (4 to 12 liters per hour). The pump effluent is diverted to waste.

The foregoing description is offered for illustrative purposes only, and the invention is not intended to be limited to the exact construction and operation shown and described. Numerous modifications and variations will be readily apparent to those skilled in the art, while still falling within the spirit and scope of the invention as claimed hereinbelow.

What is claimed is:

1. An apparatus for the continuous and substantially current measurement of the pH of a fluid in a process stream conduit using a glass electrode not in contact with said process stream and entailing a minimal loss of process fluid, said apparatus comprising:
    an enclosed sample conduit extending laterally from said process conduit to divert therefrom a portion of said fluid, said portion completely filling said sample conduit, with means in the wall of said sample conduit for receiving the pH-sensing surface of said electrode in fluid-tight relation to said wall, the portion of said wall facing said pH-sensing surface having a contour approximately complementary in shape to said surface with a gap therebetween of less than about 0.5 cm on the average and substantially smaller than the diameter of said sample conduit, the diameter ratio of said process conduit to said sample conduit ranging from about 5:1 to about 50:1, and
    means for drawing said stream through said conduit at a controlled steady rate.

2. An apparatus according to claim 1 in which said gap is from about 0.05 cm to about 0.3 cm on the average.

3. An apparatus according to claims 1 or 2, in which said fluid is a suspension and said pH-sensing surface of said electrode is bulb-shaped.

4. A method for the continuous and substantially current measurement of the pH of a stream of fluid in a process stream conduit using a glass electrode in a non-intrusive manner and entailing a minimal loss of process fluid, said method comprising:
    drawing a portion of said stream at a controlled steady rate into an enclosed sample conduit extending laterally from said process conduit, said sample conduit containing the pH-sensing surface of said electrode enclosed therein, the diameter ratio of said process conduit to said sample conduit ranging from about 5:1 to about 50:1, said portion completely filling said sample conduit,
    passing said portion through a passage within said sample conduit defined by the pH-sensing surface of said electrode and an opposing face of said conduit wall having a contour approximately complementary in shape to said surface with a gap therebetween of less than about 0.5 cm on the average and substantially smaller than the diameter of said sample conduit, and
    detecting the signal generated by said electrode.

5. A method according to claim 4 in which the flow rate of said portion through said sample conduit is from about 2 to about 40 liters per hour.

6. A method according to claim 4 in which the flow rate of said portion through said sample conduit is from about 4 to about 20 liters per hour.

7. A method according to claim 4 in which the flow rate of said portion through said sample conduit is from about 4 to about 12 liters per hour.

8. A method according to claims 4, 5, 6, or 7 in which said gap is from about 0.05 cm to about 0.3 cm on the average.

* * * * *